US00PP13524P3

(12) United States Plant Patent
Strickland

(10) Patent No.: US PP13,524 P3
(45) Date of Patent: Jan. 28, 2003

(54) OAK TREE NAMED 'QNFTA'

(75) Inventor: Thomas Julian Strickland, Statesboro, GA (US)

(73) Assignee: Tree Introductions, Inc., Bishop, GA (US)

( * ) Notice: Subject to any disclaimer, the term of this patent is extended or adjusted under 35 U.S.C. 154(b) by 0 days.

(21) Appl. No.: 09/845,026

(22) Filed: Apr. 27, 2001

(65) Prior Publication Data

US 2002/0162149 P1 Oct. 31, 2002

(51) Int. Cl.[7] ..... A01H 5/00

(52) U.S. Cl. ..... Plt./225

(58) Field of Search ..... Plt./225

*Primary Examiner*—Bruce R. Campell
*Assistant Examiner*—Susan B. McCormick
(74) *Attorney, Agent, or Firm*—Klarquist Sparkman LLP

(57) ABSTRACT

An Oak tree named 'QNFTA' having a dense branching pattern and consistent red-orange-yellow fall color and also capable of being reproduced reliably using vegetative cuttings.

8 Drawing Sheets

LATIN NAME OF THE GENUS AND SPECIES OF THE PLANT CLAIMED

*Quercus nuttallii.*

VARIETY DENOMINATION

'QNFTA'.

BACKGROUND OF THE INVENTION

The present invention relates to a new and distinct variety of oak tree which is believed to be a variety of *Quercus nuttalli*. My new variety has been given the varietal name 'QNFTA.'

I discovered my new tree in 1995 as a chance seedling growing in a cultivated area of a nursery in Statesboro, Ga.

The parentage of this tree is unclear. It is definitely a red oak type tree. Representative species include Pin Oak (*Quercus palustris*) or Red Oak (*Quercus rubra*). There are also several related species, including Nutall Oak (*Quercus nuttalli*), Shumard Oak (*Quercus shumardii*), and Scarlet Oak (*Quercus coccinea*). My new tree has characteristics and a history that have prevented making an exact identification of its species, but Nutall Oak appears to be the closest.

Nutall Oak, as well as most other red oak types, readily hybridizes with one another, and there is a high probability that this tree is a result of a cross between a Nutall Oak and Shumard Oak or some other species of red oak, since Nutall Oaks and Shumard Oaks overlap one another across much of their range. For example, in Texas, Nutall Oak is found in the lower Southeast corner of Texas, Shumard is located in a wide band covering most of the eastern part of the state, and Texas Red Oak (*Quercus texana*) is the primary tree in the central part of the state east of Dallas. There is also a large swath of habitat between the primary Shumard Oak and Texas Red Oak regions where the predominate tree is a hybrid between Shumard Oak and Texas Red Oak. Hybrids are common and can easily make up a large population of the trees in any given area.

Origin of Tree

Seeds were collected from a group of three trees in Birmingham, Ala. The seeds were collected in fall of 1991 and planted into seedbeds in late winter of 1992. In spring of 1993, 1200 bare-root liners from these planted seeds were transplanted to a nursery field. In January of 1998, the original tree of my new variety was moved to an observation site in Oconee County, Ga. where it has remained since that time.

The original tree has displayed characteristics resembling Nutall Oak as well as Shumard Oak. There is much confusion over the exact identification of this tree and several experienced individuals have expressed differing opinions. The only consistency has been the opinion that the acorn is generally the most distinguishing characteristic determining the species difference between Nutall Oak and Shumard Oak. When compared to the above oaks, the acorns on my new tree most resemble Nutall Oak, which indicates that the tree is most likely a Nutall Oak or at least has Nutall Oak as one of its parents. Other physical characteristics of the tree, such as leaf size, sinus depth or bud features, do not provide definitive answers as to the true parentage of the tree.

BRIEF SUMMARY OF THE INVENTION

As I observed the original tree of my new variety, the uniqueness of this tree became apparent because of a dense branching pattern and consistent red-orange-yellow fall color. These characteristics distinguish my new tree from other Nutall Oaks of which I am aware.

Propagation

In 1995, this original tree of my variety was successfully propagated by vegetative cuttings at my direction, and the progeny have thus far proven to retain the dense branching pattern and consistent red-orange yellow fall color of the parent tree, even as smaller plants.

Use

I observed this tree of my new variety for a period of time and believe it is particularly useful as a specimen or for grouping in lawns, parks, golf courses, commercial landscapes, and as a street tree. It provides good shade, is a relatively fast grower, adapts well to various planting conditions, and has good structural integrity. It also provides interest with its red-orange-yellow fall color.

Industry Representation

Cultivated Nutall Oak, as far as I am aware, is represented in the industry solely by seedling material. Seedling material has a wide range of variability. My new tree has dense branching pattern and consistent red-orange-yellow fall color not represented by any other Nutall Oak tree cultivar known to me.

Background

Typical Shumard Oak and Nutall Oak trees are pyramidal trees that become more spreading with age. Nutall Oak trees typically develop a fuller head at a younger age and can maintain a central leader as compared to typical Shumard Oak trees. My new tree has an upright pyramidal shape, but I expect it to become more spreading with age as is typical of the species. My new tree has a full head and central leader that is more typical of a Nutall Oak tree. Both Shumard Oak and Nutall Oak typically reach 40 to 60 feet high and wide in the landscape, but can reach 100 feet or more in nature. The ultimate height and width of new variety is not known.

Fixed Traits

My new variety has been asexually propagated by vegetative cuttings at my direction. Asexual reproduction was accomplished in Bulloch County, Ga. This propagation and observation of the resulting progeny have proven the characteristics of my new variety to be firmly fixed and reproduce true to type. Furthermore, these observations have confirmed that my new variety represents a new and improved variety of oak tree which appears to be a variation of Nutall Oak trees based upon observations of acorns in the parent tree and as particularly evidenced by the dense branching pattern and consistent red-orange-yellow fall color and which can reliably be asexually propagated using vegetative propagation.

BRIEF DESCRIPTION OF THE DRAWINGS

The accompanying photographs depict the color of the tree and foliage of my new variety as nearly as is reasonably possible to make the same in a color illustration of this character.

FIG. 3 is a close up of two single leaves depicting the upper side of leaves from a tree of my new variety.

FIG. 4 is a close up of two single leaves depicting the under side of leaves from a tree of my new variety.

FIG. 5 is a close up of typical fall leaf color of my new variety.

FIG. 8 is a close up of two acorns of my new variety.

DETAILED BOTANICAL DESCRIPTION

My 'QNFTA' variety of oak tree is currently growing at an observation site in Oconee County, Ga. It is located in an area of Oconee County that has a clay loam soil type and receives an average of 50 inches of rainfall per year. Oconee County is in USDA Hardiness Zone 7. Both Shumard Oak and Nutall Oak are hardy in USDA Zones 5 through 9.

The observed tree was approximately nine years old. The time of root initiation was about four to eight weeks from time of sticking.

My new tree has not been observed under all growing conditions, and thus, variations may occur as a result of different growing conditions. The following is a detailed description of my new variety of oak tree with color terminology in accordance with The Royal Horticultural Society (R.H.S.) color chart published by The Royal Horticultural Society in London. The observations are of the original tree growing at the observation site in Oconee County, Ga.

Taxonomy

Figure 1:
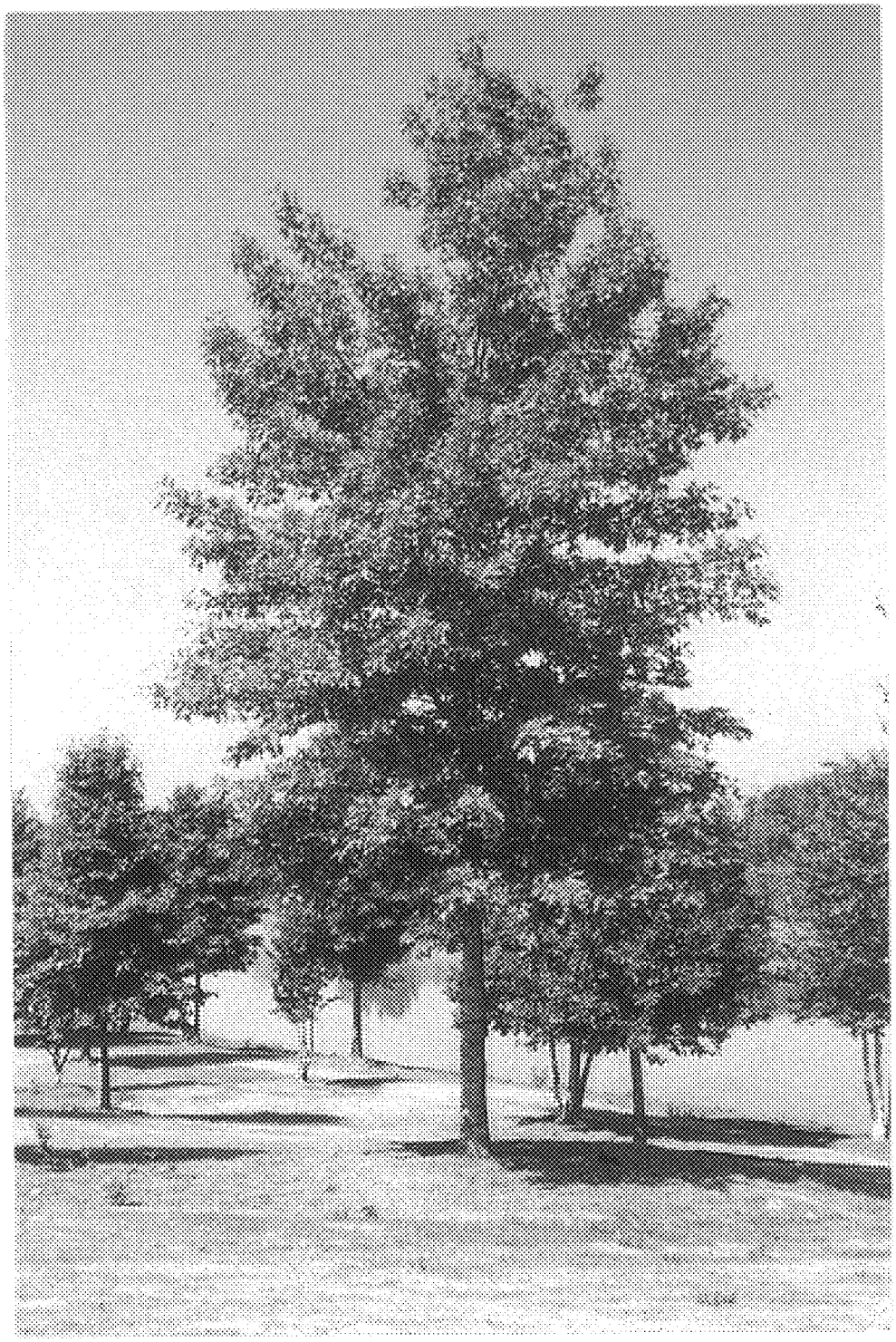
FIG. 1 is a photograph of the original tree of my new variety in summer leaf.

My new tree has an upright-pyramidal shape (FIG. 2), but I expect it to become more spreading with age as is typical of the species. My new tree has a full head (FIG. 1) and a central leader that is more typical of a Nutall Oak. The original tree is currently 10 inches in caliper at 12 inches above the ground after about nine years. The original tree is currently about 27 feet high and 18 feet wide with a height to width ratio of 1.44. Prior to transplanting to the observation site, the original tree had an average growth in caliper of about 0.9 inches to about 1.1 inches per year. The progeny also have displayed a similar growth rate.

Figure 6:
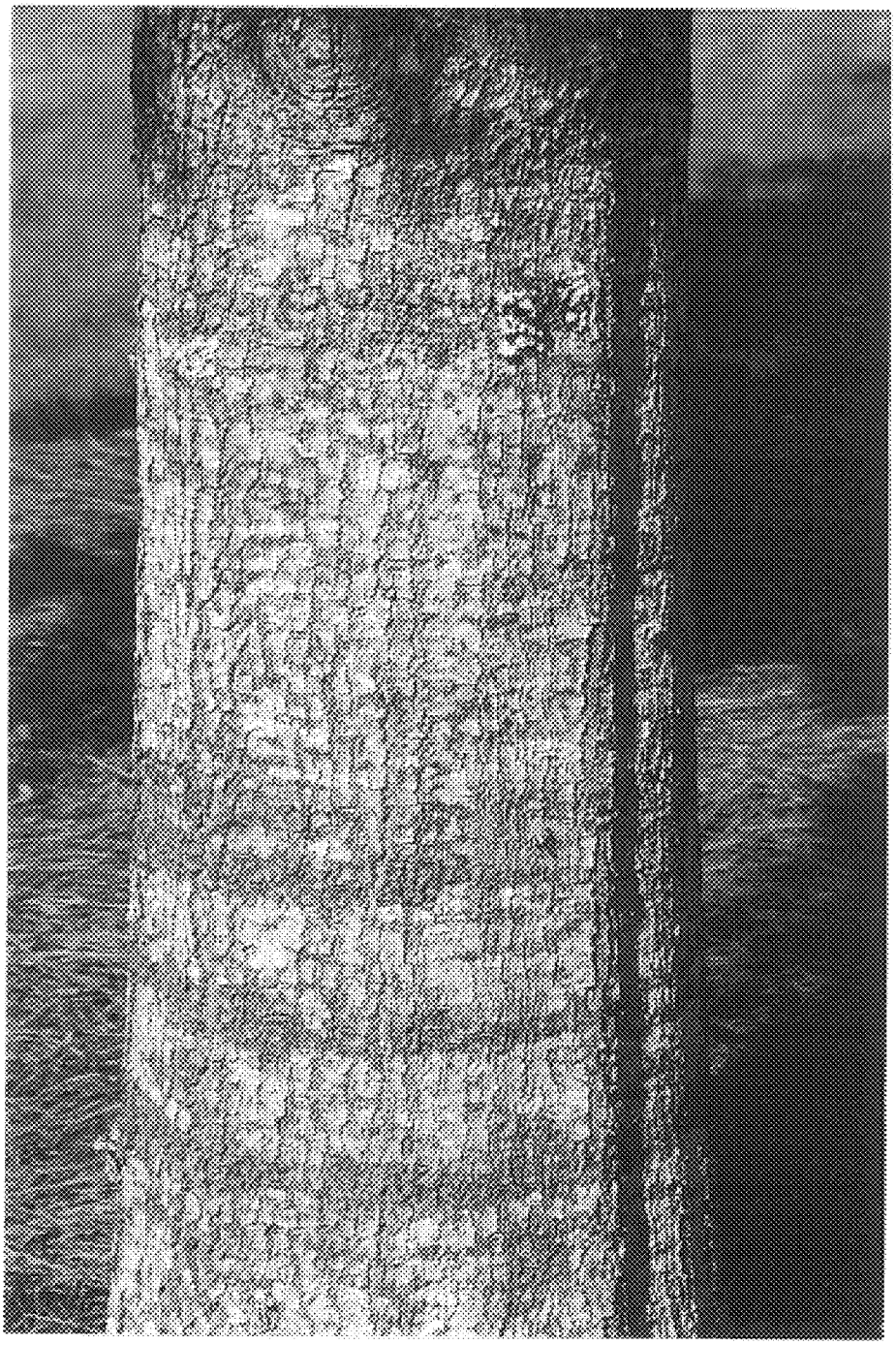
FIG. 6 is a close up of the trunk of the original tree.

The bark of my new tree is typical of the species (FIG. 6). In youth, the bark is smooth and with age develops shallow ridges and furrows. The color of the bark is typical of the species, exhibiting light gray (RHS 156D) and grayed-green (RHS 195A) patches and striations.

Figure 2:
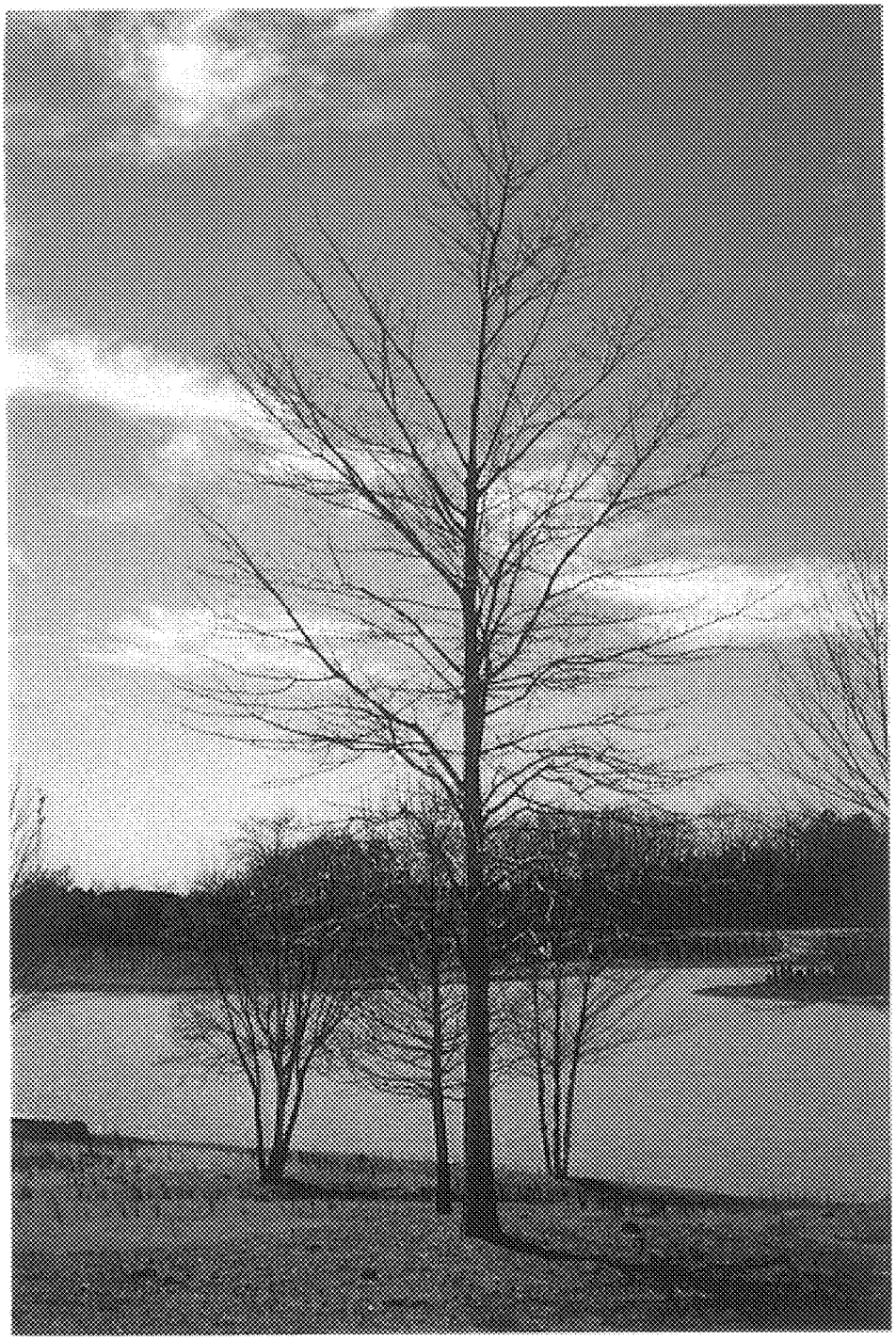
FIG. 2 is a photograph of the original tree of my new variety during winter.
Figure 7:
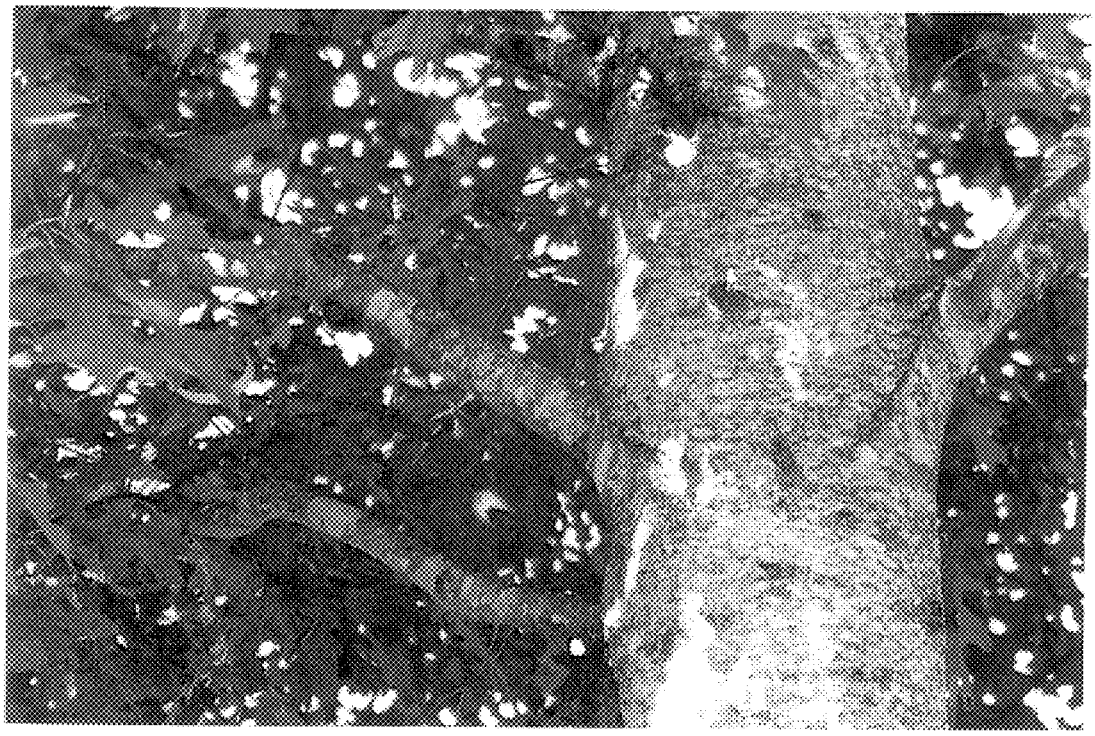
FIG. 7 is a close up of the branching habit of my new variety.

The branching is somewhat upright compared to most other seedlings (FIG. 2 and FIG. 7). Branches emerge from the trunk at about a 45-degree angle.

Figure 3:
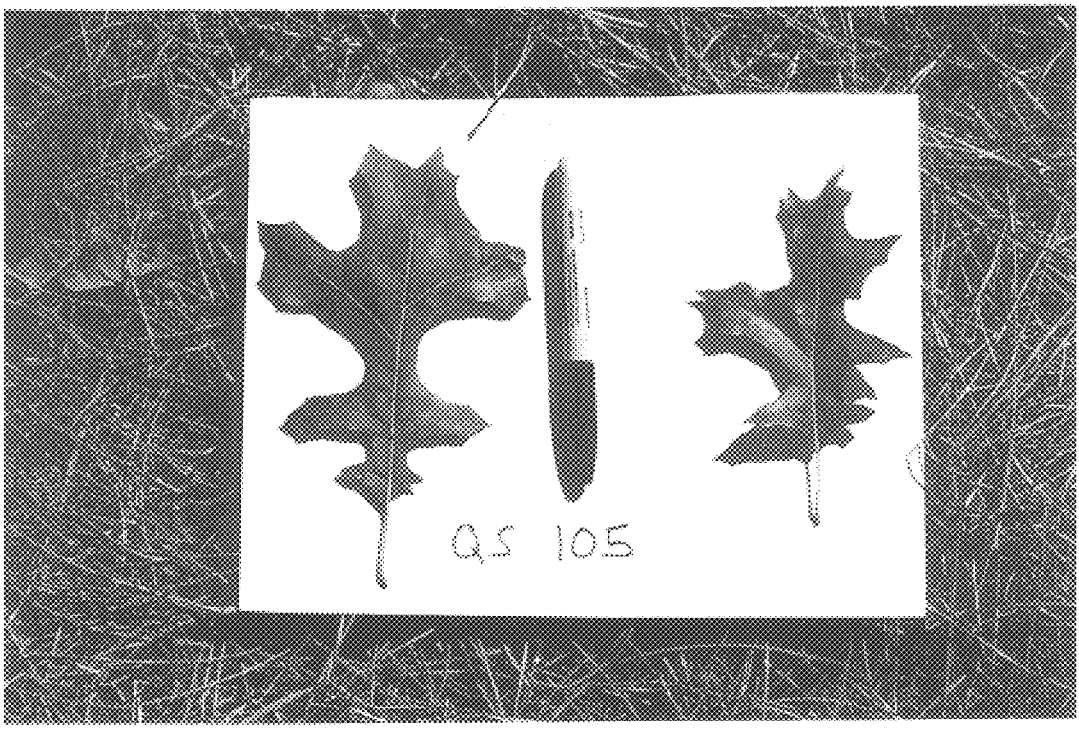
In FIGS. 3–5 and 8, the term "QS 105" relates to an earlier, alternative identifier of the 'QNFTA' variety, but is not intended to be the varietal name. As stated above, the denomination for this variety is 'QNFTA'.
Figure 4:
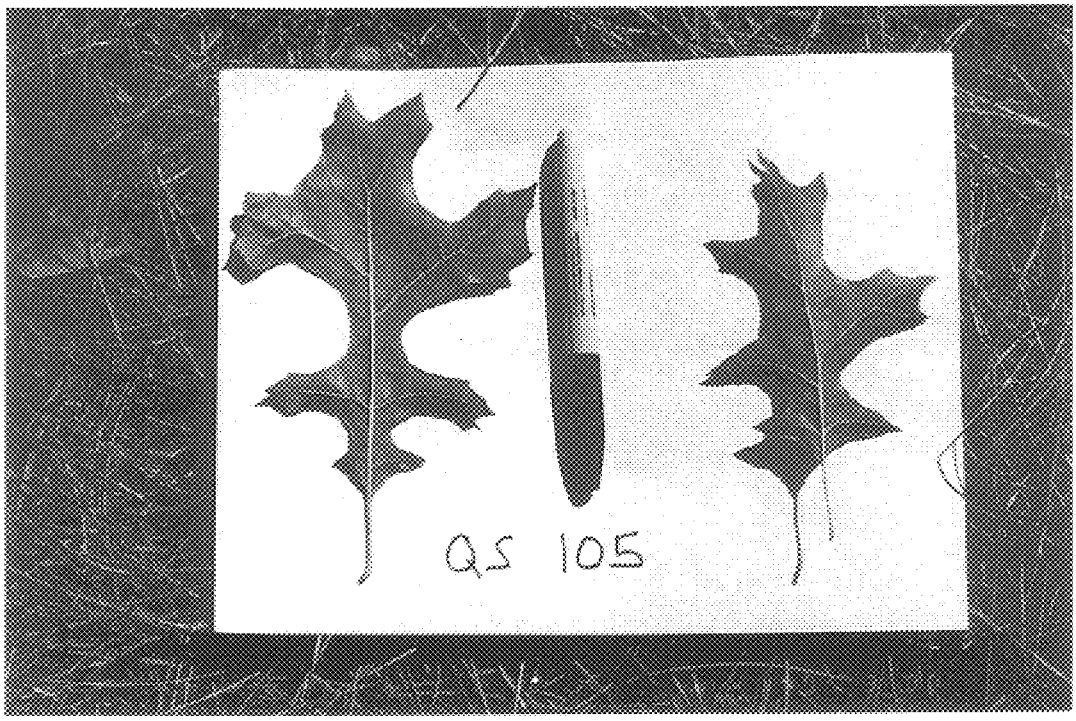
Figure 5:
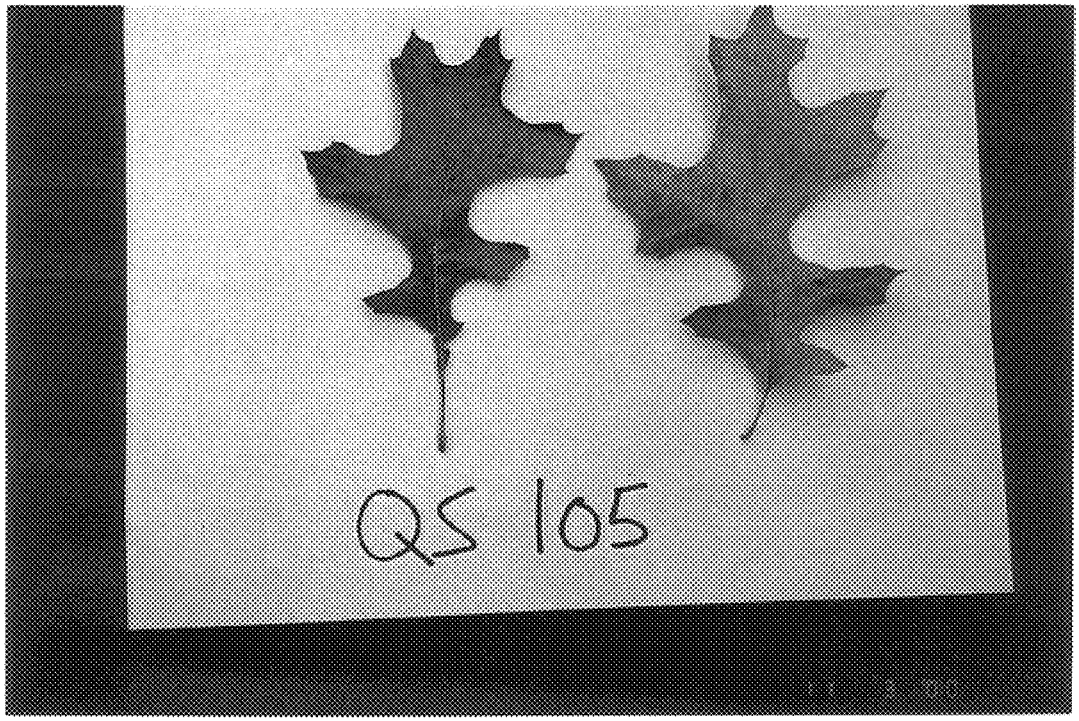

The leaves of Nutall Oak, Shumard Oak, and Pin Oak all resemble one another, and my tree has leaves typical of the species *Q. nuttalli* in size and shape: Alternate, simple, obovate to elliptic, 4 to 9" long, 2 to 5" wide, with 5 to 9 lobes (FIG. 3). Sinuses are rounded with narrow lobes. Leaves maintain a dark green color in the summer. The upper leaf surface (FIG. 3) is a dark green in the summer (RHS 139A), and the lower leaf surface at this time (FIG. 4) is a lighter green (RHS 141B). The veins are a green-yellow (RHS 145A). My new tree has consistent fall color which ranges from red (RHS 42C) to orange (RHS 25B) to yellow (RHS 7A) (FIG. 5).

Buds are typical of the species, being imbricate, ⅛ to ¼" long, ash gray to brown-gray, pubescent with ciliate scale margins.

Most oaks have flowers so similar that it is difficult to distinguish between species based on flower type. The flowers of my new tree are typical of most oaks. The trees are monoecious. The staminate catkins are pendent and clustered. The individual flowers comprise a 4- to 7-lobed calyx that encloses 6 to 12 stamens. Pistillate flowers are solitary or in few to many-flowered spikes from the axils of the new leaves. Individual distillate flowers consist of a 6-lobed calyx surrounding the ovary, with the whole partly enclosed in an involucre.

Figure 8:
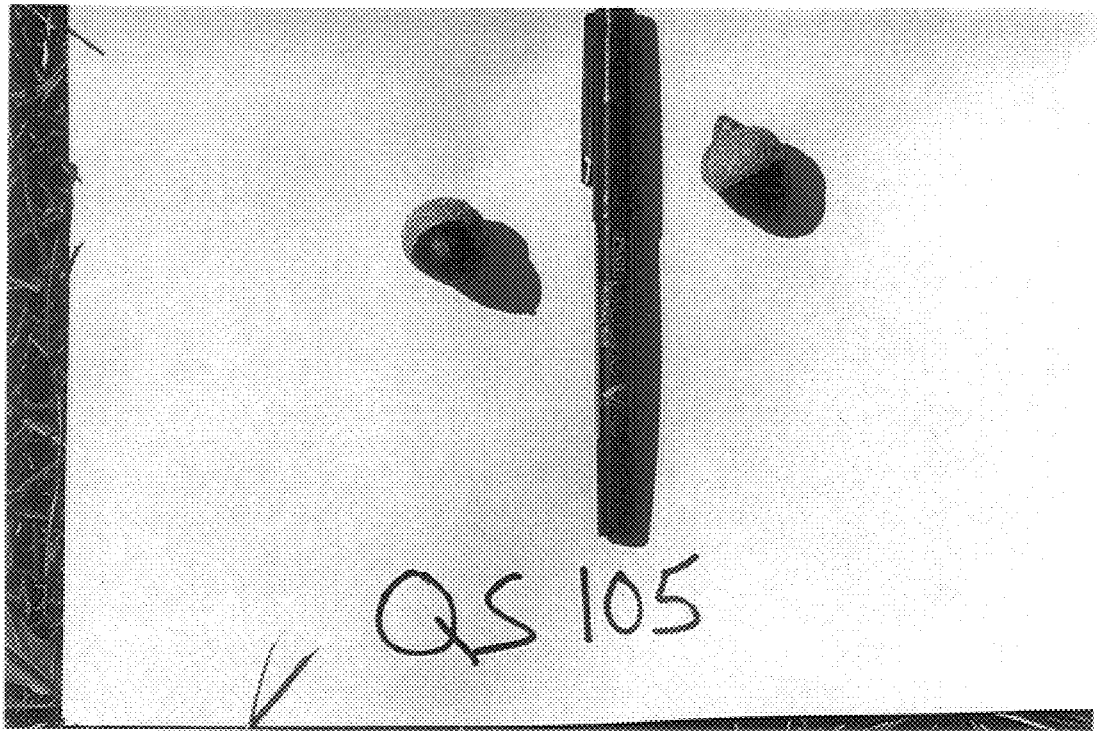

The acorns for my new tree most closely resembles that of Nutall Oak. In this case, they are typical of the species. Acorns are ovate, ¾ to 1¼" long, short-stalked, oblong-ovoid and covered ⅓ to ½ by the cap (FIG. 8). The acorn is grayed-orange in color (RHS 177A) with dark brown (RHS 200B) striations. The cap is light brown (RHS 199B). The acorn is the best identifying feature to discriminate Nutall Oak from Shumard Oak. Shumard Oak has an acorn of approximately the same size and shape, though sometimes Shumard acorns are more ovate, as compared to Nutall Oak. However, in Shumard Oak, the cap covers only the top part of the acorn, and the striations are more pronounced. The root system is typical of the species, fibrous and somewhat shallow.

Origination: Selected as a chance seedling in a field at a nursery in Statesboro, Ga. The parentage of this tree is believed to include Nutall Oak, but is not entirely clear for reasons explained above.

Tree shape: Upright-pyramidal with a full head and central leader.

Trunk: Central leader.

Bark: Typical of the species. Smooth in youth. Mature Bark: Develops shallow ridges and furrows. Color light gray (RHS 156D) and grayed-green (RHS 195A) patches and striations.

Branches: The branching is somewhat upright compared to most other seedlings (FIG. 2 and FIG. 7). Branches emerge from the trunk at about a 45-degree angle. Branches are about ¼" in diameter, with a smooth texture, and gray-green (RHS 194A) in color. Internode length ranges from about ¾" to about 1⅞".

Leaves: Typical of the species *Q. nuttalli* in size, texture and shape. Alternate, simple, obovate to elliptic, 4 to 9" long, 2 to 5" wide, with 5 to 9 lobes. Glabrous. Sinuses are rounded with narrow lobes. Summer leaf upper surface color is dark green (RHS 139A), summer leaf lower surface color is lighter green (RHS 141B) and fall color is red-orange-yellow (RHS 42C, 25B, 7A). Apex shape is acuminate and base shape is cuneate. Venation pattern is pinnate. Petiole is dull green (RHS 152B) in color, approximately 7/16 inches to 9/16 inches long and about 1/16 inch in diameter.

Buds and flowers: Typical of the species, being imbricate, ⅛ to ¼" long, ash gray to brown-gray, pubescent with ciliate scale margins. For the observed trees growing in Oconee County, Ga., flowering begins about April 5 to April 10 and extends for about 10 to 14 days.

Flowers: Typical of the species. Staminate catkins are pendent and clustered. The individual flowers comprise a 4- to 7-lobed calyx that encloses 6 to 12 stamens. Pistillate flowers are solitary or in few to many-flowered spikes from the axils of the new leaves. Individual distillate flowers consist of a 6-lobed calyx surrounding the ovary, with the whole partly enclosed in an involucre.

Fruit: Typical of *Q. nuttalli*. Acorns are ovate, ¾" to 1¼" long, about ½" to ⅝" wide, smooth in texture, short-stalked, oblong-ovoid and covered one-third to one-half by the cap. The acorn is grayed-orange in color (RHS 177A) with dark brown to black striations (RHS 200B). The cap is light brown (RHS 199B).

Root system: The root system is typical of the species, fibrous and somewhat shallow.

Winter hardiness: Observed to be hardy in at least USDA Zone 7.

Drough/heat tolerance: Observed to be tolerant to drought and heat conditions of a region from north Georgia to central Florida.

I claim:

1. A new and distinct variety of Oak tree substantially as herein shown and described, characterized particularly as to novelty by its unique dense branching pattern and consistent red-orange-yellow fall color.

* * * * *

UNITED STATES PATENT AND TRADEMARK OFFICE

CERTIFICATE OF CORRECTION

PATENT NO. : PP 13,524 P3
DATED : January 28, 2003
INVENTOR(S) : Thomas Julian Strickland It is certified that error appears in the above-identified patent and that said Letters Patent is hereby corrected as shown below:

Column 2,
Line 40, change “red-orange yellow.” to -- red-orange-yellow --

Column 6,
Line 30, change “Drough” to -- Drought --

Signed and Sealed this

Sixteenth Day of September, 2003

JAMES E. ROGAN
*Director of the United States Patent and Trademark Office*